Figure 1:
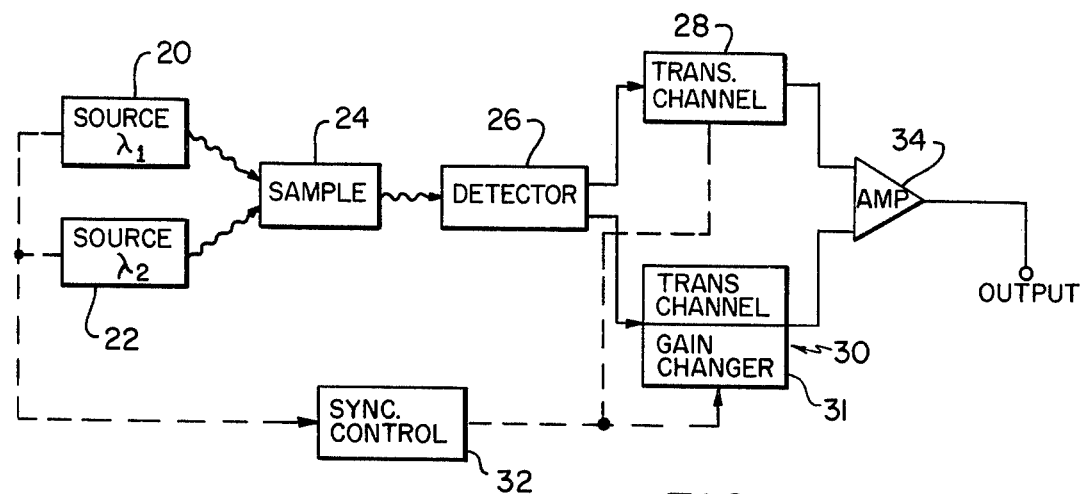

United States Patent [19]

Hirschfeld

[11] 4,100,416
[45] Jul. 11, 1978

[54] SERUM FLUORESCENCE SUPPRESSION

[75] Inventor: Tomas R. Hirschfeld, Framingham, Mass.

[73] Assignee: Block Engineering, Inc., Cambridge, Mass.

[21] Appl. No.: 773,546

[22] Filed: Mar. 2, 1977

[51] Int. Cl.² ............... G01N 21/38; G01N 33/16; G01J 3/30

[52] U.S. Cl. ............... 250/461 B; 356/39; 356/85

[58] Field of Search ............... 250/461 R, 461 B, 302; 356/39, 85

[56] References Cited

U.S. PATENT DOCUMENTS

| | | | |
|---|---|---|---|
| 3,433,952 | 3/1969 | Howerton | 250/461 B X |
| 3,918,812 | 11/1975 | Holm | 250/461 B X |
| 3,973,129 | 8/1976 | Blumberg et al. | 250/461 B |

*Primary Examiner*—Alfred E. Smith
*Assistant Examiner*—Janice A. Howell
*Attorney, Agent, or Firm*—Schiller & Pandiscio

[57] ABSTRACT

A system for suppressing normal serum fluorescence in fluorescence immunoassay, in which in one embodiment, the immunoassay fluorescently tagged reaction product in a single sample is irradiated at a first wavelength which will excite fluorescence from the tagged product and then at a different wavelength which is not substantially in an absorption band of the fluorescent tag, the respective fluorescent emissions being detected and converted to electrical signals. The difference between the signals, adjusted for variation in serum fluorescence at the two wavelengths, is a function of the antigen titer. In an alternative form, the sample is irradiated at the first wavelength for a predetermined period of time commencing very shortly after the emission reaction is started, and the resulting signal from the detector is differentiated. In both instances, output signal due to serum fluorescence per se is suppressed.

10 Claims, 3 Drawing Figures

U.S. Patent  July 11, 1978  4,100,416

SERUM FLUORESCENCE SUPPRESSION

This invention relates to detection and measurement of small quantities of chemical compounds or compositions, and specifically to the detection and measurement of such compounds and compositions through fluorescence immunoassay with a reduced background.

Immunoassay techniques are based upon the well known immune reaction, i.e. the extremely specific reaction between an antibody and its antigen or hapten. The antibodies can be used to assay antigens through the antibody reaction in a large variety of ways, as by precipitation or agglutination or by coupling to a tracer or to a fixed substrate, and the like. When either an antibody or its antigen is tagged with a fluorescent material or dye, the immunoassay technique can be used to determine the presence of untagged material through the antibody/antigen reaction. For example, where an antibody is tagged with a fluorescent tracer material and reacted with a solution containing an unknown quantity of antigen, the antigen titer can be readily determined by measuring the distribution of the fluorescently tagged or labeled antibody between that bound to antigen and that unbound.

A problem in immunoassay is separating the reacted components from the unreacted tagged material, so that the strength of the desired signal from the former can be readily equated with the titer of the unknown substance, but a number of techniques are known to effect separation. This separation problem becomes complicated with the antigenic material which one seeks to assay is in a blood serum solution. The latter is known to contain a very large variety of different molecular materials which are fluorescent so that when exposed to narrow band excitation over a wide spectrum, the serum will nonetheless fluoresce brightly. Where the antigen is present in small quantities and even if all of the fluorescently tagged antibody unreacted with antigen has been removed, the fluorescent background provided by the serum itself in response to radiant excitation of the fluorescently tagged antibody will tend to swamp the desired signal.

One attempted solution to this problem is to measure the background or serum fluorescence at a given excitation wavelength prior to adding tagged antibody to the serum sample and subtracting that background from the resulting signal obtained after the immunoassay reaction has taken place and the unreacted tagged antibody has been separated. This technique however, has not been particularly successful in solving the problem because the background fluorescence is, inter alia, a function of the amount of serum present and there are substantial problems in providing exact duplicate aliquots of the original serum and of the serum which contains the antibody/antigen reaction product. Additionally, the serum fluorescent signal is usually so much greater than the signal due to the fluorescence of the tagged immunoassay reaction product that the difference between the two measurements (which is the desired signal) may be lost in the statistical noise or variation in the serum fluorescence. Lastly, it will be apparent that for every assay attempted by this prior art technique, two separate samples must be prepared in each case and measurements taken with respect to each of the separate samples.

A principal object of the present invention is therefore to provide a system for discriminating a fluorescent immunoassay product from background serum fluorescence with a high degree of accuracy from but a single sample or specimen. To this end, the present invention comprises a system for assaying fluorescently tagged antibody-antigen reaction product in blood serum in a single specimen, in which system fluorescence is excited in the specimen and two different measurements are made of the fluorescent emission. A difference is determined between the two measurements and the amount of the reaction product in the serum is determined as a function of the measured difference. In one specific embodiment, the sample or specimen of blood serum containing the reaction product is irradiated first at a wavelength which is in the absorption band of the fluorescent tag coupled to the reaction product and therefore the fluorescence from the specimen is due to that emitted by the excited tag molecules and also from the components of the serum which are also excited by that wavelength. The same sample is then irradiated at a second wavelength which is not (or poorly) absorbed by the tag molecules so that the fluorescent emission from the specimen can be attributed almost entirely to excitation of serum components. It is appreciated that, even if the two wavelengths are relatively close to one another, the intensity of the fluorescence due solely to the serum will be slightly different by a scaling factor which however remains substantially constant for a given type of blood serum except under circumstances as will be described hereinafter. By adjusting the two measurements according to the scaling factor and determining the difference between them, it will be seen that if no antibodyantigen reaction product is present to provide fluorescence, the difference will be zero because clearly none of the signal has been contributed by the fluorescence of such reaction product. On the other hand, if reaction product is present, the signal is readily determined with a high degree of accuracy as will be described hereinafter. The intensity of the difference signal thus determined is of course proportional to the total number of fluorescent tags and therefore can be correlated readily with the concentration or amount (hereinafter generally referred to as "amount") of the antigen being assayed.

In yet another embodiment of the present invention, the serum sample containing an unknown titer of antigen has added thereto a known amount of fluorescently tagged antibody, the reaction product is irradiated with excitation stimulus in an absorption band of the tag, and the fluorescent emission measured at a first time. The same sample reaction product is then irradiated at a second or later time and again the fluorescence is measured. From the two measurements, the change in signal strength with time or its derivative $ds/dt$ can be determined. Because the reaction of antigen with antibody follows an exponential law, from the derivative one can determine therefore what the total amount of reaction product will be. It will be seen that the fluorescence due to serum (being a constant for the single sample for that excitation wavelength at the two different times) when diffrentiated will disappear from the computation.

In both of the embodiments described, it will be apparent that the technique employed is to observe the signal due only to the fluorescently tagged material while excluding the fluorescence due to the serum, all from a single sample, thereby obviating the problem of matching aliquots.

Other objects of the present invention will in part be obvious and will in part appear hereinafter. The invention accordingly comprises the apparatus and method possessing the construction, combination of elements, and arrangement of parts which are exemplified in the following detailed disclosure, and the scope of the application of which will be indicated in the claims.

Figure 2:
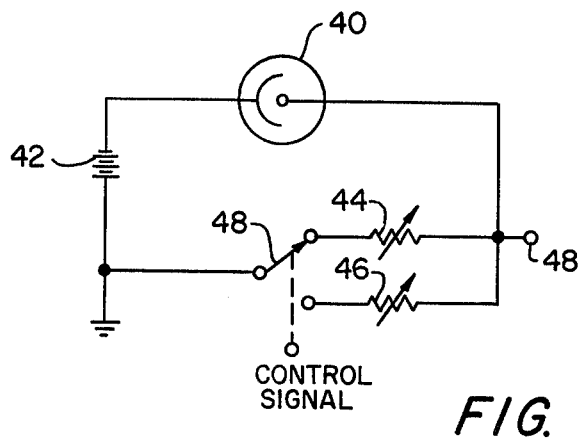
Figure 3:
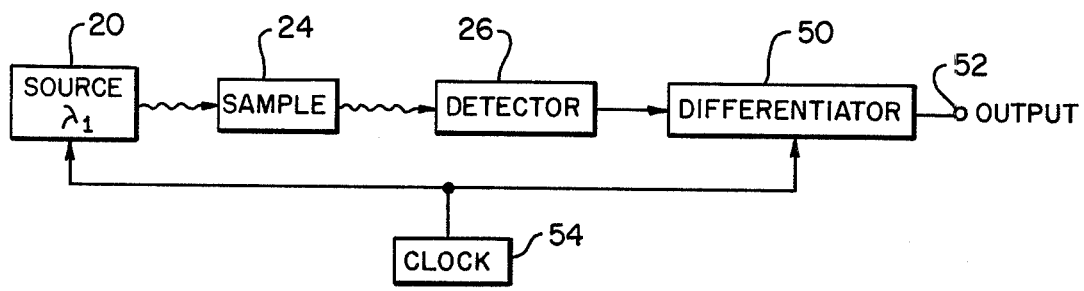

For a fuller understanding of the nature and objects of the present invention, reference should be had to the following detailed description taken in connection with the accompanying drawings wherein:

FIG. 1 wherein there is shown a block diagram of apparatus forming one embodiment of the system of the present invention; and FIG. 2 is a diagram of a portion of a preferred form of part of the embodiment of FIG. 1; and FIG. 3 is a block diagram of yet another embodiment of the system of the present invention.

The present invention is not to be considered limited to the assay of protein antigens only, but is clearly applicable to the assay of biological cells and cellular parts as well as non-proteinaceous materials which can be attached to a protein and are known as haptens. Consequently, the term "antigen" as used hereinafter in the specification and claims is intended to generically refer to antigens and haptens as well.

The principles of the present invention can be advantageously understood by considering the following: a blood serum sample is treated by any of a large number of prior art techniques to produce a reaction product between a particular antigen and the antibody specific thereto, which antibody has been tagged or labeled with one or more fluorescent dye molecules. The blood serum sample and reaction product are then irradiated at a first wavelength $\lambda_1$ in the absorption band of the dye so that the sample will then fluoresce. For the sample, ignoring unreacted tagged antibody which can be considered removed or otherwise deactivated by any of a number of known techniques, one can define S = the intensity in photoelectrons of the fluorescence arising from the serum per se; and T = the intensity in photoelectrons of the fluorescence arising from the excited tagged dye; and N = the noise.

The total fluorescent intensity $M_1$ observed when the sample is irradiated at $\lambda_1$ is $$M_1 = (S + T) \pm N \qquad (1)$$

If the same sample is then irradiated with a second wavelength $\lambda_2$ which is substantially outside of an excitation band of the dye, the serum fluorescence S' then observed is $$S' = aS \qquad (2)$$

where "$a$" is substantially a proportionality constant. Similarly, the dye fluorescent T' upon excitation at $\lambda_2$ is $$T' = bT \qquad (3)$$

where $b$ is another proportionality constant which, because $\lambda_2$ is outside of an absorption band of the dye and therefore excites little or no fluorescence, approaches or is zero and can be neglected. The total fluorescent intensity $M\lambda_2$ observed when the sample is irradiated at $\lambda_2$ is $$M\lambda_2 = (aS + bT) \pm N' \qquad (4)$$

Since the two measurements are taken on exactly the same sample, the terms are correlated. Hence, if one takes the difference between the two signals $M_1$ and $M_2$, one obtains $$\frac{M\lambda_2}{a} - M_1 = T(1 - \frac{b}{a}) \pm N'' \qquad (5)$$

Note then that the difference in the two signals is proportional only to the signal from the tagged dye molecules.

If one computes the noise equivalent sample concentration, i.e. the value of RMS concentration required to produce an RMS signal-to-noise ratio of unity, for the output signal $M\lambda_1$ as expressed in equation (1) and computes a similar noise equivalent sample concentration for the difference signal expressed in equation (5), it can be shown that the latter provides an improvement by a factor of approximately 80 in the signal-to-noise ratio over the former.

Apparatus for carrying out the technique just described is shown in FIG. 1 which includes a first and second sources 20 and 22 respectively of radiation at the foregoing wavelength $\lambda_1$ and $\lambda_2$. Sources 20 and 22 can be implemented in a number of devices. For example, the two sources may be provided by a single argon laser, commercially available, which includes a prism at one end thereof, rotation of the prism providing two or more different output wavelengths. Similarly, sources 22 and 20 can be formed from typically a broad band radiation source such as a carbon arc or the like and a pair of filters mounted for rotation to alternately intersect a beam of light from the broad band source. In yet another embodiment, sources 20 and 22 can be formed of a single source such as a mercury lamp for providing an output beam, in the path of which is disposed an interference filter mounted on a torsional tuning fork. As the tuning fork moves the interference filter so that the angle of incidence of the beam from the mercury lamp is harmonically changed, the output of the filter will similarly change from one wavelength to another at the extremeties of the motion of the tuning fork. Of course, in the simplest version, sources 20 and 22 are discrete sources such as a pair or lasers, or broad band sources with appropriate filtering.

Radiation at wavelengths $\lambda_1$ and $\lambda_2$ are alternately directed upon a serum sample containing the reaction product of the desired tagged antibody-antigen reaction, all shown generally at 24. As heretofore noted, a number of known techniques may be used to separate the unreacted tagged antibody from the reaction product. For example, the competition binding technique taught in U.S. Pat. No. 3,939,350 may be used. In the latter patent, the sample chamber is bounded by a totally internally reflecting cell (also known as an ATR or attenuated total reflection cell) and the antigen or an antigen analog is chemically bound to the ATR cell surface. The sample or specimen of blood serum to be assayed is then placed into the sample chamber and a known amount of fluorescently tagged antibody (preferably less than the amount of antigen bound to the ATR cell surface) is added to the blood serum sample. The amount of antibody reacting with the antigen bound to the ATR cell surface will vary according to the competition provided by the unknown amount of antigen present in the specimen. If one now irradiates the ATR cell at a wavelength in an absorption band of the fluorescent dye, an evanescent wave is created with a few hundred angstroms extending from the ATR interface into the serum. The statistically significant fluorescence which occurs is that of the tagged antibody reacted with the antigen bound to the ART cell surface, and background fluorescence due to untagged antibody is statistically negligible.

The fluorescence from the blood serum sample at 24 is detected by photodetector 26 which may be any of a very large number of devices such as photomultipliers, photovoltaic devices and the like. Detector 26 generates an electrical signal which is proportional to the intensity of the radiation detected. Of course the detector is selected so as to be responsive to at least a narrow band of output radiation across the emission spectrum from sample 24.

The output of detector 26 is preferably fed along a pair of transmission channels 28 and 30 which are respectively activated substantially in synchronism with the operation of respective sources 20 and 22, at least one of channels 28 and 30 including a amplitude scaler or gain changer 31, typically an operational amplifier or the like, which adjusts the amplitude of the signal transmitted by the channel according to some factor, which in this instance, is preferably the proportionality factor "$a$" described in equation (2). Alternatively, in place of channels 28 and 30, a signle channel could be employed, the output signals from detector 26 corresponding to excitation by wavelength $\lambda_1$ and $\lambda_2$ being separated in time. In the latter instance, then the gain in the channel would be changed in synchronism with the operation of sources 20 and 22 to apply the requisite proportionaly factor "$a$" to the proper signal.

As means for synchronizing the transmission of channels 28 and 30, synchronizing control 32 is provided and can be a very simple mechanism. For example, where sources 20 and 22 are formed of a single broad band source and a rotating filter pair, the filter can be rotated by a synchronous motor. The input AC wave form driving the synchronous motor then is, after appropriate shaping and amplification is necessary, employed to actuate electronic switches or gates controlling access to respective channels 28 and 30. In such instance, the synchronous motor, AC wave form source and gates would constitute the particular synchronous control 32.

The output of transmission channels 28 and 30 are coupled to the input of differential amplifier 34, the output signal from the latter being the difference between the amplitude of the two input signals thereto.

In a particularly desirable form of the embodiment of FIG. 1, detector 26 is a photoemissive transducer or phototube 40 with the usual electron-emitting cathode and an anode which collects electrons emitted by the cathode when the anode is at a positive potential (provided by battery 42) with respect to the cathode. When phototube 40 is illuminated, a current flows in an external circuit and produces an output voltage across a load resistor. In the form shown in FIG. 2, a pair of variable resistances (or potentiometers if desired) 44 and 46 are provided as load resistors in series with the anode of phototube 40, resistors 44 and 46 being selectively and alternatively switched into the circuit by switch 48. The latter of course is controlled by a synchronizing signal provided by synchronous control 32. The values of resistances provided by the two load resistors provide the desired proportionality factor. It will be appreciated that the two load resistors essentially constitute the pair of transmission channels described in connection with FIG. 1.

The output from the circuit of FIG. 2 appearing at terminal 48 will be seen (assuming that sources 20 and 22 are alternatively actuated and synchronously switch 48 alternately switches between resistors 44 and 46) to be a signal somewhat in the form of a unipolar repetitively varying signal. Thus, the signal appearing at output 48 can be applied to the input of a known peak-to-peak detector, such as differential amplifier 34, to yield the desired signal proportional to the fluorescent output from the tagged reaction product.

It will be appreciated that for a particular biological type of blood serum (e.g. from a given species), normally the value of the proportionality factor "$a$" can be easily determined or set into the system by providing the serum per se as sample 24 and operating the system while adjusting the values of resistors 44 and 46 to give a null peak-to-peak signal. However, if the blood serum is taken from an organism which has ingested a substantial amount of medication or a drug such as terramycin or the like, the serum fluorescence due to the presence of the drug will frequently be an order of magnitude or greater than the normal serum fluorescence so that the setting of the gain in transmission channels 28 and 30 should then be recalibrated for that particular serum.

In one example of the operation of the invention described in connection with FIG. 1, typically the two sources 20 and 22 are provided by a mercury lamp having an interference filter mounted on a torsional tuning fork as previously described, thereby providing two different output bands of radiation centered respectively around 546 nm and 577 nm. In such case, the sample is formed of blood serum containing the reaction product of an antigen and an antibody which has been conjugated with tetramethyl rhodamine isothiocyanate. The dye absorbs well at 546 nm, but substantially all of the fluorescence observed when the sample is irradiated at 577 nm will arise from the serum itself.

In yet another example, using an argon laser with a prism as sources 20 and 22, the output from the laser is alternated between radiation centered respectively around 4880 Å and 5145 Å. The dye conjugated to the antibody in the reaction produce in sample 24 is fluorescein isothiocyanate which fluoresces substantially only in response to the 4880 Å radiation.

In yet another embodiment of the present invention, the two measurements made on the same sample, instead of being fluorescent measurements taken at different wavelengths are fluorescent measurements taken from excitation of the reaction product at an absorption wavelength of the latter, but at two different times during the formation of the reaction product. In most prior art fluorescence immunoassay techniques, the usual course is to mix the tagged antibody with the suspected titer of antigen, wait until the reaction has substantially gone to completion (which may be several hours or more) and then after separation of the reaction product from the unreacted tagged material, irradiation of the reaction product and measurement of the fluorescent emissive output. However, this technique is slow and, as previously pointed out requires that separate measurements be made on two distinct aliquots in order to obtain a measure of the serum fluorescence as background. The present invention as shown in the embodiment disclosed in FIG. 3 obviates many of these difficulties.

The embodiment of FIG. 3 includes a source 20 of radiation at a wavelength $\lambda_1$ intended to be in the absorption band of a dye radicals coupled to the antibody to be used to assay for the specific antigen in sample 24. As in the embodiment of FIG. 1, the apparatus includes detector 26 positioned to observe the fluorescent output from sample 24 when the latter is irradiated with the output of source 20. The output of detector 26 is coupled to the input of differentiator circuit 50. The latter can be any of the large number of either analog or digital differentiating circuits well known in the art such as a differentiating operational amplifier or the like. Differentiator 50 provides at its output 52 a signal which is the derivative with respect to time of the input signal from detector 26.

Clock means, typically a square wave oscillator or the like shown at 54, is coupled to both source 20 and differentiator 50 to synchronously initiate operation thereof and to terminate operation thereof after a precisely determined time interval.

In operation of the embodiment shown in FIG. 3, a specimen solution the antigen-titer of which it is desired to assay, is placed in sample chamber 24 and an antigen-antibody reaction in which the reaction product is fluorescently tagged, is initiated. Preferably, immediately thereafter, clock 54 is started and turns on both source 20 and differentiator circuit 50 for a predetermined period of time, e.g. several seconds to several minutes. The clock then turns off source 20 and differentiator circuit 50.

One would expect that the fluorescent signal from chamber 24 in FIG. 3 would arise basically from three sources: the serum fluorescence, fluorescence from the reaction product of the antigen-antibody reaction, and fluorescence from the unreacted fluorescent dye radicals. In order to distinguish between fluorescence from the reacted and unreacted dye radicals, a number of known techniques can be used, but a preferred technique is to employ a method such as that described in connection with U.S. Pat. No. 3,939,350. In such case then the fluorescent emission seen by detector 26 in FIG. 3 will arise almost entirely from both the serum per se and from the reaction product of the antigen-antibody reaction. The latter reaction being on a molecular level in solution, occurs at a rate governed by Brownian diffusion dynamics and hence is a logarithmic function somewhat in the form $e^{\pm kt}$ where $t$ is a time interval and $k$ is a factor dependent, inter alia, upon the concentration or amount of antigen present in the specimen solution. Of course, the concentration remains constant during the measurement although part of the antigen may be bound and part may be unbound by antibody. Hence, the fluorescent emission detected by detector 26 has three components: the serum fluorescence, the fluorescence due to the tagging dye radicals and a small noise component which is basically the shot noise of the system.

It will be remembered that the measurement is preferably taken immediately after the antibody-antigen reaction is initiated so that the change in fluorescence due to the antibody-antigen reaction is proceeding at a maximum rate. Because the serum fluorescence per se however does not change but remains substantially constant and the derivative of a constant is zero, the contribution of the serum fluorescence to the output signal from differentiator 50 also approaches zero. If one considers that the average noise over the period of time $t_1 - t_0$ during which clock 54 has kept source 20 on, the noise can also be considered to be substantially constant so that its contribution to the output signal from differentiator 50 is negligible, at least to a first approximation.

Because the fluorescent signal due to emission from the fluorescent tab it is $e^{\pm kt}$, then the output signal from differentiator 50 due to the fluorescent tag emission is then $\pm ke^{\pm kt}$. As noted, this output signal is a function of concentration of the antigen, and can readily be calibrated.

Since certain changes may be made in the above process and apparatus without departing from the scope of the invention herein involved, it is intended that all matter contained in the above description shall be interpreted in an illustrative and not in a limiting sense.

What is claimed is:

1. Apparatus for assaying fluorescently-tagged antibody-antigen reaction product contained in a specimen of blood serum, said apparatus comprising in combination:
    means for irradiating said specimen with first radiation in the absorption band of the tag of said product so as to stimulate fluorescent emission from said tag;
    means for separately irradiating said specimen with second radiation substantially incapable of stimulating fluorescent emission from said tag;
    means for detecting fluorescent emission from said specimen due to irradiation of said specimen with said first radiation so as to provide a first electrical signal;
    means for detecting fluorescent emission from said specimen due to irradiation of said specimen with said second radiation so as to provide a second electrical signal;
    means for scaling said first and second signals with respect to one another by scaling factor; and
    means for producing as a function of a difference between said first and second signals as scaled, an electrical output signal related to the amount of said antigen in said specimen.

2. Apparatus as defined in claim 1, wherein said scaling factor is the ratio between the amplitude of signals corresponding to the fluorescent emission from said blood serum, in the absence of said reaction product, when said serum is respectively irradiated by said first and second radiations.

3. Apparatus as defined in claim 1 wherein said means for irradiating said specimen with said first and second radiation comprises a laser capable of providing output radiation alternatively centered around at least two different wavelengths.

4. Apparatus as defined in claim 1 wherein said means for irradiating said specimen with said first and second radiation comprises a source of radiation, an interference filter and means for varying the angle at which radiation from said source is incident on said filter.

5. Apparatus as defined in claim 1 wherein said means for irradiating said specimen with said first and second radiation comprises a source of radiation at least two different passband filters and means for alternating transmission of radiation from said source through each of said filters.

6. Apparatus as defined in claim 1 wherein said means for producing said output electrical signal comprises a differential amplifier.

7. Apparatus for assaying fluorescently-tagged antibody-antigen reaction product contained in a specimen of blood serum, said apparatus comprising in combination:
    means for irradiating said specimen with first radiation in the absorption band of the tag of said product so as to stimulate fluorescent emission from said tag;

means for detecting said fluorescent emission and for providing an electrical signal responsively thereto; and means for differentiating said electrical signal so as to provide an output signal which is a function of the amount of antigen in said specimen.

8. Method for assaying fluorescently-tagged antibody-antigen reaction product contained in a specimen of blood serum, said method comprising the steps of:

stimulating fluorescent emission from said specimen by irradiating said specimen separately with a first beam of radiation capable of stimulating fluorescent emission from the fluorescent tag of said product, and with a second beam of radiation which is substantially capable of stimulating fluorescent emission from said serum but is not capable of stimulating fluorescent emission from said tag;

taking at least two different measurements of said emission respectively due to irradiation of said specimen by said first and second beams, and deriving from said measurements an electrical output signal which is a difference signal between said measurements, said output signal being a function of the amount of antigen in said specimen.

9. Method for assaying fluorescently-tagged antibody-antigen reaction product contained in a specimen of blood serum, said method comprising the steps of stimulating fluorescent emission from said specimen by irradiating said specimen with radiation capable of stimulating fluorescent emission from the fluorescent tag of said product, and during the reaction which produces said product, while said reaction is at a relatively early stage, taking at least two measurements respectively at a first time $t_0$ early in said stage and a second time $t_1$ later in said stage; and deriving from said measurements an electrical output signal as the derivative of the change in said measurement over the time interval $t_1 - t_0$, said output signal being a function of the amount of antigen in said specimen.

10. Method as defined in claim 9 including the step of scaling said measurements with respect to one another by a scaling factor derived from the relative intensities of fluorescent emission from said blood serum due to irradiation by said first and second beams in the absence of said reaction product.

* * * * *